(12) United States Patent
Ikeda et al.

(10) Patent No.: US 8,054,081 B2
(45) Date of Patent: Nov. 8, 2011

(54) RESIDUAL GAS ANALYZER

(75) Inventors: Toru Ikeda, Kyoto (JP); Junji Aoki, Kyoto (JP); Kotaro Takijiri, Kyoto (JP)

(73) Assignee: Horiba STEC, Co., Ltd., Kyoto (JP)

( * ) Notice: Subject to any disclaimer, the term of this patent is extended or adjusted under 35 U.S.C. 154(b) by 256 days.

(21) Appl. No.: 12/294,888

(22) PCT Filed: Mar. 9, 2007

(86) PCT No.: PCT/JP2007/054703
§ 371 (c)(1),
(2), (4) Date: Nov. 13, 2008

(87) PCT Pub. No.: WO2007/111110
PCT Pub. Date: Oct. 4, 2007

(65) Prior Publication Data
US 2010/0134116 A1    Jun. 3, 2010

(30) Foreign Application Priority Data
Mar. 27, 2006    (JP) ................. 2006-086136

(51) Int. Cl.
*G01N 27/62*    (2006.01)
(52) U.S. Cl. ........................................ 324/464
(58) Field of Classification Search ............ 324/464; 702/85
See application file for complete search history.

(56) References Cited

U.S. PATENT DOCUMENTS

| | | | |
|---|---|---|---|
| 3,718,029 A * | 2/1973 | Gourdine et al. | 73/28.02 |
| 5,857,890 A * | 1/1999 | Ferran | 445/67 |
| 6,333,632 B1 * | 12/2001 | Yang et al. | 324/464 |
| 2005/0086017 A1 * | 4/2005 | Wang | 702/85 |

FOREIGN PATENT DOCUMENTS

| | | | |
|---|---|---|---|
| JP | 10/142198 | | 5/1998 |
| JP | 281671 | * | 5/1998 |
| JP | 10142198 | * | 5/1998 |
| JP | 11/014614 | | 1/1999 |
| JP | 2003/281671 | | 10/2003 |
| JP | 2003/294619 | | 10/2003 |
| WO | 90/15658 | | 12/1990 |
| WO | 2005/040985 | | 5/2008 |

OTHER PUBLICATIONS

Ikeda, T., "Pressure Master RGA", Horiba Technical Reports, Readout No. 28, 5 pages, Mar. 2004.
ISA Japan, International Search Report of PCT/JP2007/054703, Jun. 12, 2007, JPO.

* cited by examiner

*Primary Examiner* — Jeff Natalini
(74) *Attorney, Agent, or Firm* — Alleman Hall McCoy Russell & Tuttle LLP (57) ABSTRACT

Provided is an excellent residual gas analyzer, which can perform measurements while being suitably arranged even in small areas, such as those in semiconductor equipments, and can perform measurements for display of measurement results without an external personal computer. The analyzer is provided with a sensor unit having a sensor section for detecting a residual gas; an operating section for receiving operation for controlling the sensor section; a residual gas analysis processing section for processing analysis of the residual gas based on the output from the sensor section; and an analysis processing result screen display section for displaying on a screen the analysis processing results obtained from the residual gas analysis processing section. The analyzer is also provided with a device main body which can be in a mounted status wherein the sensor unit is mounted or in a removed status wherein the sensor unit is removed.

7 Claims, 14 Drawing Sheets

RESIDUAL GAS ANALYZER

FIELD OF THE INVENTION

The present invention relates to a residual gas analyzer used for a residual gas analysis or the like in a chamber of a semiconductor equipment or the like.

BACKGROUND ART

In recent years, as semiconductor devices are increasingly integrated and functionalized, deposition and etching processes are rapidly switched to corresponding dry processes.

To stably provide high quality products, real-time control is crucial to accurately grasp a state inside a chamber and keep a process in an optimum state. For this reason, a residual gas analyzer (RGA) is strongly desired.

Specifically, it is known that this type of residual gas analyzer is configured to include: a sensor unit integrally provided with a sensor part including an ion source, a mass analyzing part, and a detection part, and a spectraconverter part; and an interface part that is provided between the sensor unit and an external personal computer and cable-connected to them (see, for example, Non-patent document 1).

According to the residual gas analyzer, a residual gas introduced into the ion source first collide with thermal electrons emitted from a high temperature filament, and is consequently ionized. The generated ions are accelerated and converged by a lens to be introduced into the mass analyzing part. In the mass analyzing part, DC and AC voltages are applied to four cylindrical electrodes (quadrupole) to separate the ions by mass. The separated ions are detected as a current by a Faraday cup. The ion current is proportional to an amount of the residual gas (partial pressure), and therefore the residual gas can be measured with accuracy.

Non-patent document 1: Ultracompact residual gas analyzer "PresssureMaster RGA series", (Toru Ikeda, Special issue paper, Horiba Technical Reports, No. 28, p. 12-15, March 2004, Horiba, Ltd.)

DISCLOSURE OF THE INVENTION

Problem to be Resolved by the Invention

However, in a conventional configuration, because the sensor unit and interface part are separate bodies, it is considered that the sensor unit can be arranged in a small area of the semiconductor equipment to make a measurement; however, the measurement can only be made with the sensor unit being cable-connected to the external personal computer, and is therefore virtually limited by a fitting position of the sensor unit. Also, without the external personal computer, analysis results cannot even be displayed.

The present invention is made by focusing on such problems, and a primary object thereof is to provide an excellent gas analyzer, which can make a measurement with being suitably arranged even in the small area of the semiconductor equipment, or the like, and without an external personal computer, perform operations from the measurement to a display of a result of the measurement.

Means Adapted to Solve the Problem

That is, a residual gas analyzer according to the present invention is configured to include: a sensor unit configured to be provided with a sensor part for sensing a residual gas; and a device main body provided with an operating part for receiving an operation for controlling the sensor part, a residual gas analysis processing part for performing analysis processing of the residual gas on a basis of an output of the sensor part, and an analysis processing result screen display part for displaying on a screen a result of the analysis processing in the residual gas analysis processing part, the device main body being able to be in a mounted status where the sensor unit is mounted or in a removed status where the sensor unit is removed.

Based on such configuration, if the sensor unit is removed from the device main body, it can be arranged and used in a small area of a semiconductor equipment, which cannot contain the device as a whole. On the other hand, if the sensor unit is mounted on the device main body, the device can be independently used as a whole, and is therefore easy to handle. Also, the device does not require activation of an external device such as a personal computer to operate the sensor part, and is therefore convenient.

That is, there can be provided an excellent gas analyzer, which can make a measurement with being suitably arranged even in the small area of the semiconductor equipment, or the like, and without an external personal computer, perform operations from the measurement to a display of a result of the measurement.

To enable simultaneous measurements at a plurality of positions while ensuring the above-described effects, it is desirable that one of a plurality of sensor units is mounted on the one device main body; and the other sensor units are connected by wire or wirelessly to one device main body or one sensor unit described above so as to form a serial or a parallel connection, with being removed from the one device main body.

A desirable aspect of the sensor part of the present invention includes that the sensor part is provided with: an ion source for ionizing gas molecules; a quadrupole part for separating an ion beam obtained from the ion source, according to an ion's mass/charge ratio; and a Faraday cup detection part for capturing the ion beam separated in the quadrupole part to detect as an ion current.

If the sensor unit is provided with a spectraconverter part for converting the ion current detected in the Faraday cup detection part into a digital voltage signal indicating a voltage value, the effect of, for example, a magnet or the like provided in the semiconductor equipment can be avoided, and therefore the measurement can be made with accuracy even if the sensor unit is used with being removed from the device main body.

A desirable aspect of the operating part of the present invention includes that the operating part is an operation button provided in the device main body.

Also, to further improve usability, the operating part is desirably removable from the device main body. Further, an operating part that is a separate body from the device main body may be provided.

To simplify wiring, it is desirable that one device main body and the plurality of sensor units described above have cables capable of supplying power and making communication, and the cables are connected to a hub capable of supplying power.

Effect of the Invention

As described, regarding the residual gas analyzer according to the present invention, if the sensor unit is removed from the device main body, it can be arranged and used in the small area of the semiconductor equipment, which cannot contain the device as a whole. On the other hand, if the sensor unit is mounted on the device main body, the device can be independently used as a whole, and is therefore easy to handle. Also, the device does not require activation of an external device such as a personal computer to operate the sensor part, and therefore can be convenient.

That is, there can be provided the excellent gas analyzer, which can make a measurement with being suitably arranged even in the small area of the semiconductor equipment, or the like, and without an external personal computer, perform operations from the measurement to a display of a result of the measurement.

EXPLANATIONS OF REFERENCE NUMERALS

A: residual gas analyzer, 1: sensor unit, 11: sensor part, 12: spectraconverter part, 2: device main body, (P1): mounted status, (P2): removed status, 2B: operating part (sensor operation buttons), 2P: analysis processing result screen display part (liquid crystal panel), 111: ion source, 113: quadrupole part, and 114: Faraday cup detection part.

BEST MODE FOR CARRYING OUT THE INVENTION

One embodiment of the present invention will hereinafter be described referring to the drawings.

A residual gas analyzer A of the present embodiment is, as illustrated in FIGS. 1 to 8, configured to include: a sensor unit 1 integrally provided with a sensor part 11 for sensing a residual gas and a spectraconverter part 12 (not shown); and a device main body 2, which can be in a mounted status (P1) (see FIG. 1) where the sensor unit 1 is mounted or in a removed status (P2) (see FIG. 2) where the sensor unit 1 is removed. The respective parts are specifically described below.

Figure 1:
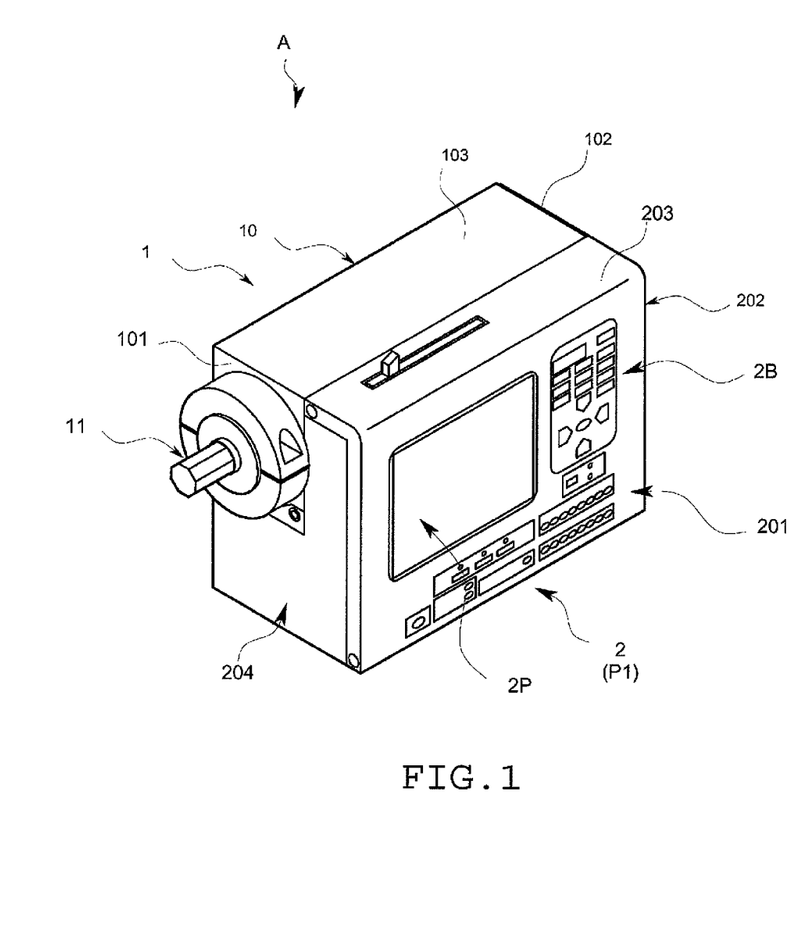
FIG. 1 is an overall perspective view illustrating a residual gas analyzer (mounted status) according to one embodiment of the present invention.

The sensor unit is, as illustrated in FIG. 1 and the other drawings, configured to provide a sensor unit case 10 of a substantially rectangular parallelepiped shape with the sensor part 11, and the unshown spectraconverter part 12, power supply, and the like. Note that, in the present embodiment, a tip side of the sensor part 11 is projected from one side wall 101 of the sensor unit case 10. Also, on the other side wall 102 of the sensor unit case 10, there is provided a connecter 1C for making a connection between the device main body 2 and the sensor unit 1 by a cable CA when the sensor unit 1 is removed from the device main body 2 (see FIG. 6). In the present embodiment, as the connecter 1C, an RS-232C connecter is used, but may be appropriately changed depending on an embodiment, such as the use of a USB connector. Further, on a bottom wall 100 of the sensor unit case 10, mounting brackets 1xa and 1xb (hereinafter collectively referred to as the mounting brackets 1x) respectively having the same cross-sectional shape are provided along a mounting direction in order to mount the sensor unit 1 on the device main body 2 (see FIG. 2).

Figure 9:
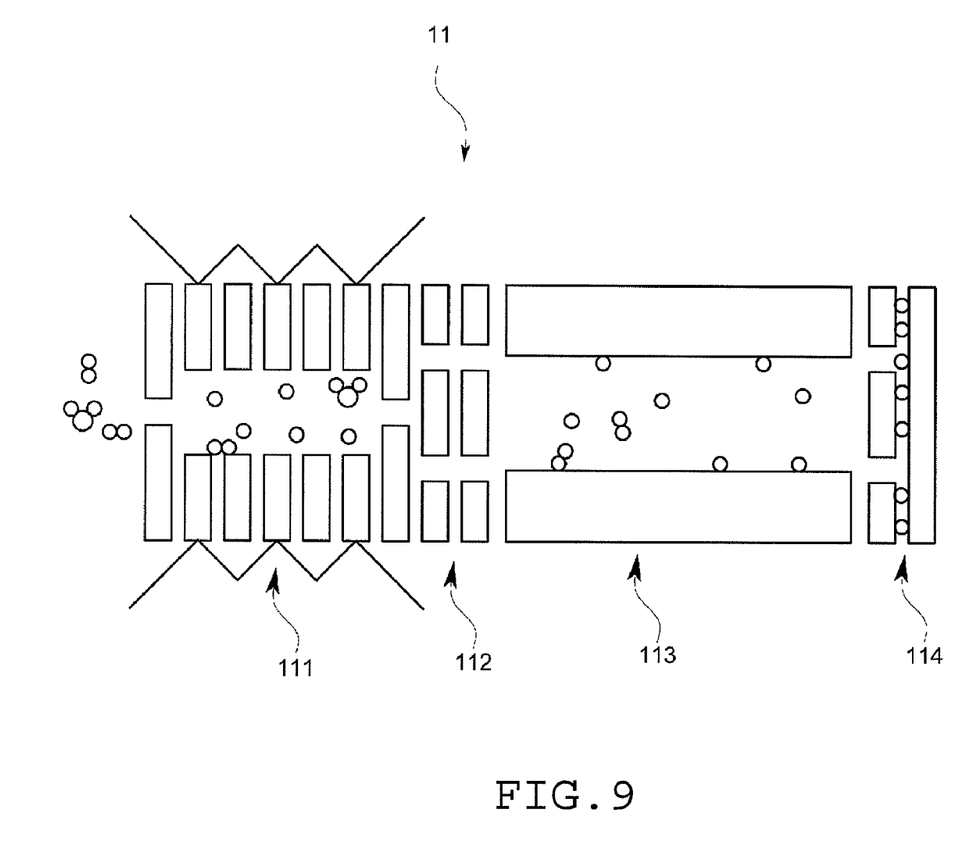
FIG. 9 is a structural cross-sectional view schematically illustrating a configuration of a sensor part in the same embodiment.

As illustrated in FIG. 9, the sensor part 11 includes: an ion source 111 for ionizing gas molecules; lens 112 for accelerating and converging an ion beam obtained from the ion source 111; a quadrupole part 113 for separating, according to an ion's mass/charge ratio, the ion beam accelerated and converged by the lens 112; and Faraday cup detection part 114 for capturing the ion beam separated in the quadrupole part 113 to detect as an ion current.

The spectraconverter part 12 is intended to convert the ion current detected in the Faraday cup detection part 114 into a digital voltage signal indicating a voltage value.

Figure 2:
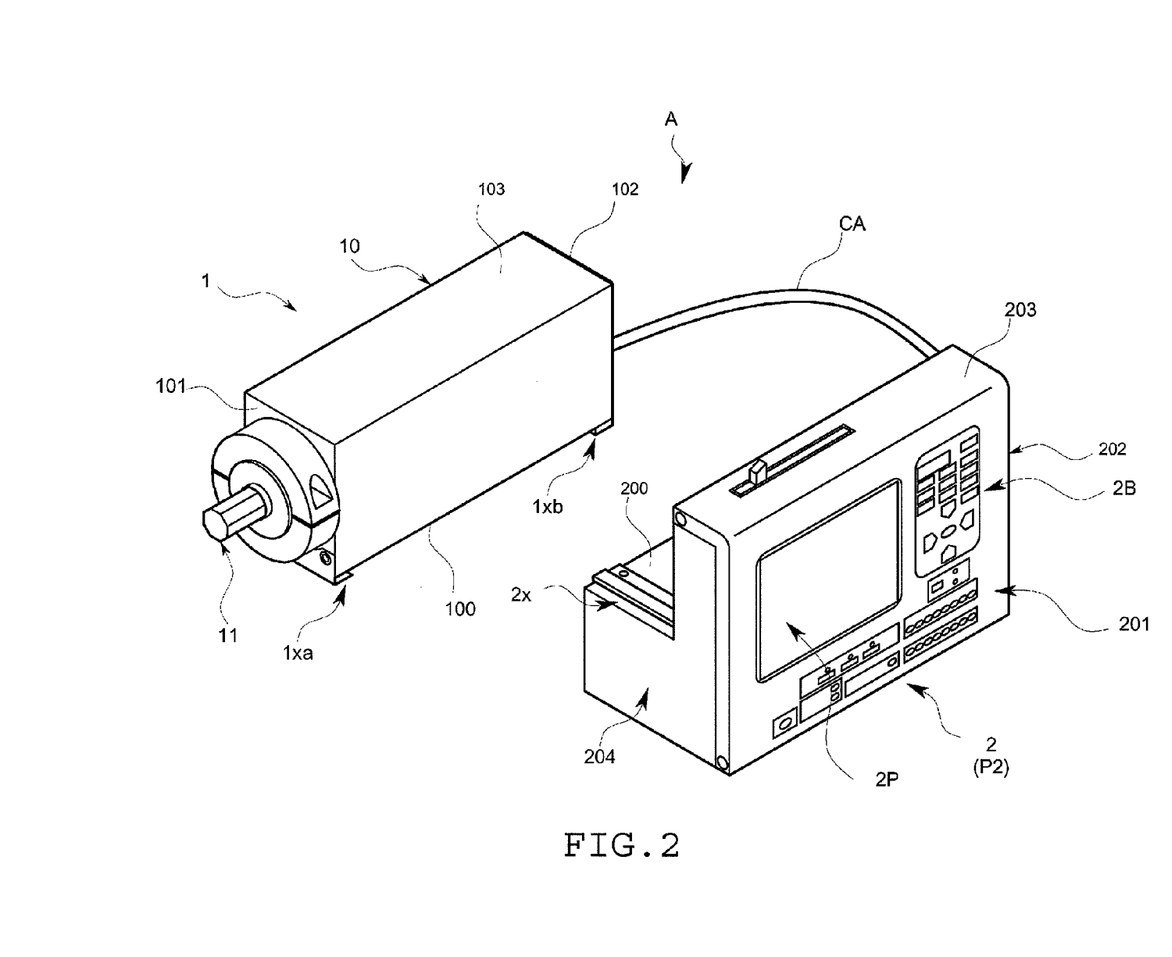
FIG. 2 is an overall perspective view illustrating the residual gas analyzer (removed status) in the same embodiment.

The device main body 2 is, as illustrated in FIG. 2 and the other drawings, of a substantially L-block shape as viewed from outside, which includes a plurality of panels such as a front panel 201 and right side panel 202, and configured to incorporate a circuit part (not shown) mounted with a CPU, an internal memory, and the like. Also, it is configured such that the CPU and peripheral devices are operated according to a program stored in the internal memory, and the device main body 2 fulfills functions as a residual gas analysis processing part for performing analysis processing of the residual gas on a basis of an output of the sensor part 11, and the like.

Figure 5:
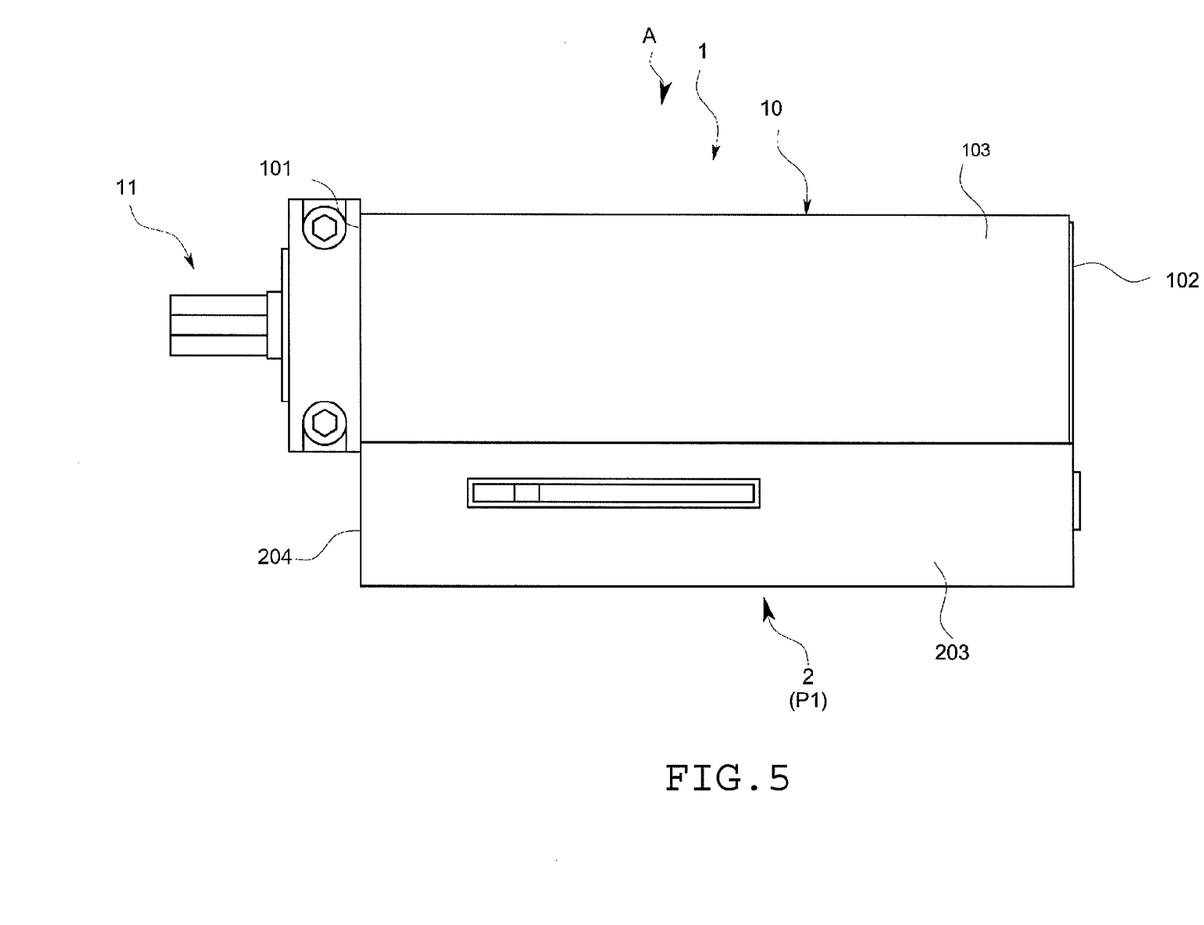
FIG. 5 is a plan view illustrating the residual gas analyzer in the same embodiment.
Figure 6:
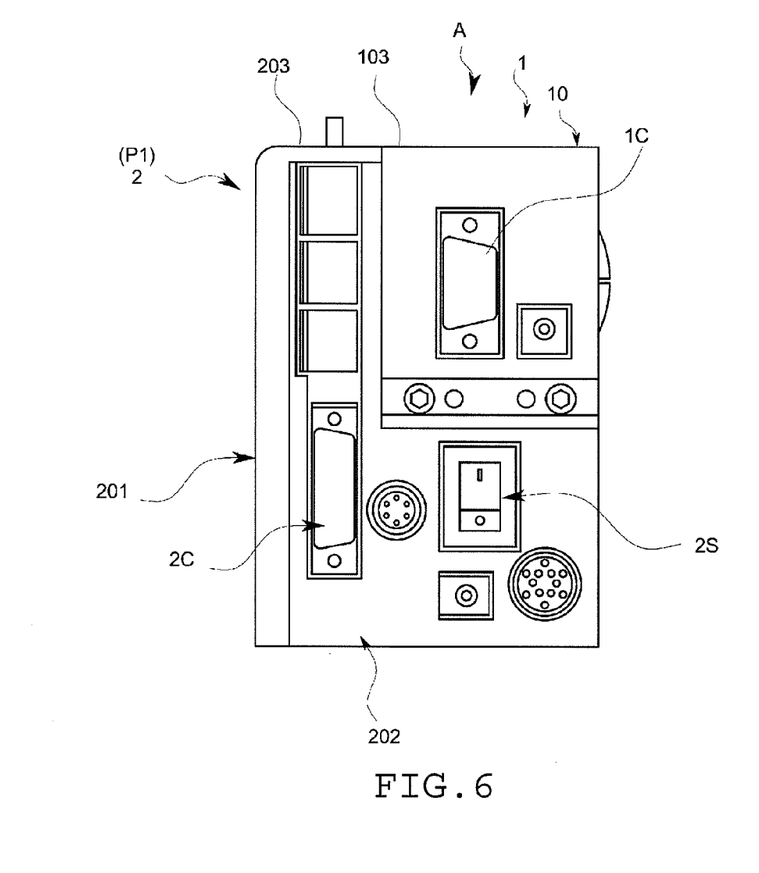
FIG. 6 is a right side view illustrating the residual gas analyzer in the same embodiment.
Figure 7:
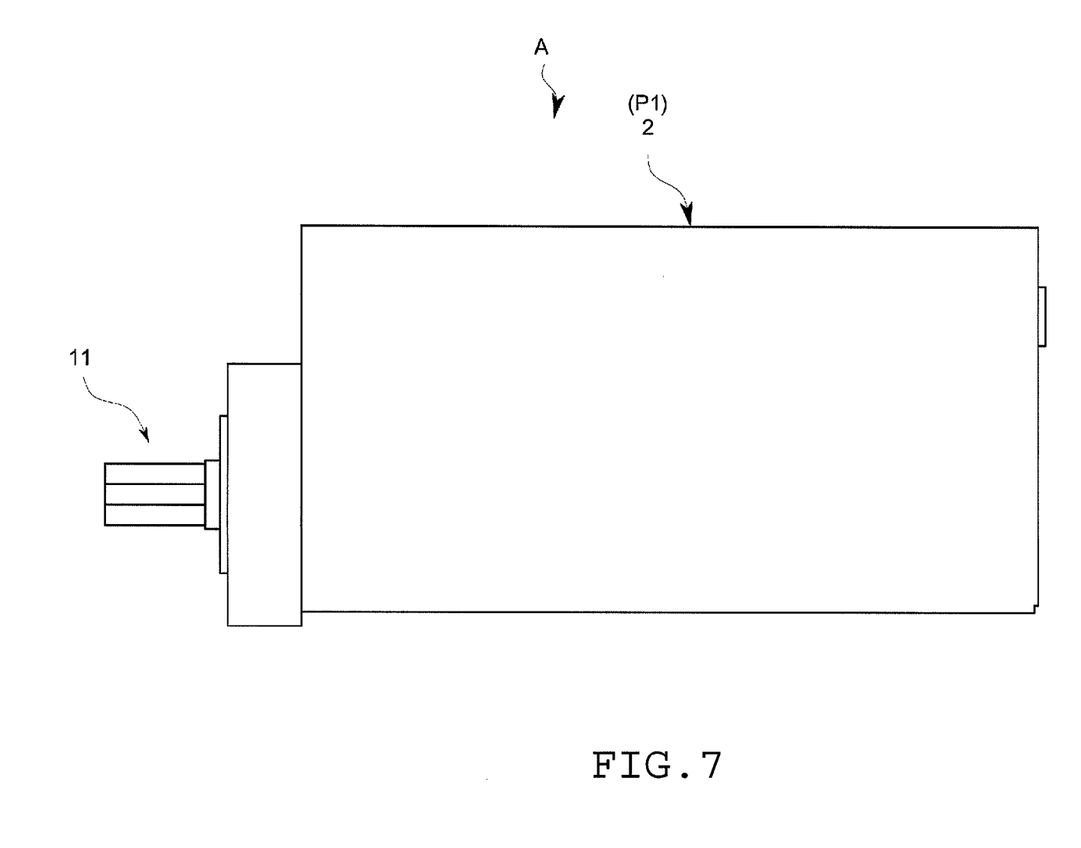
FIG. 7 is a bottom view illustrating the residual gas analyzer in the same embodiment.
Figure 8:
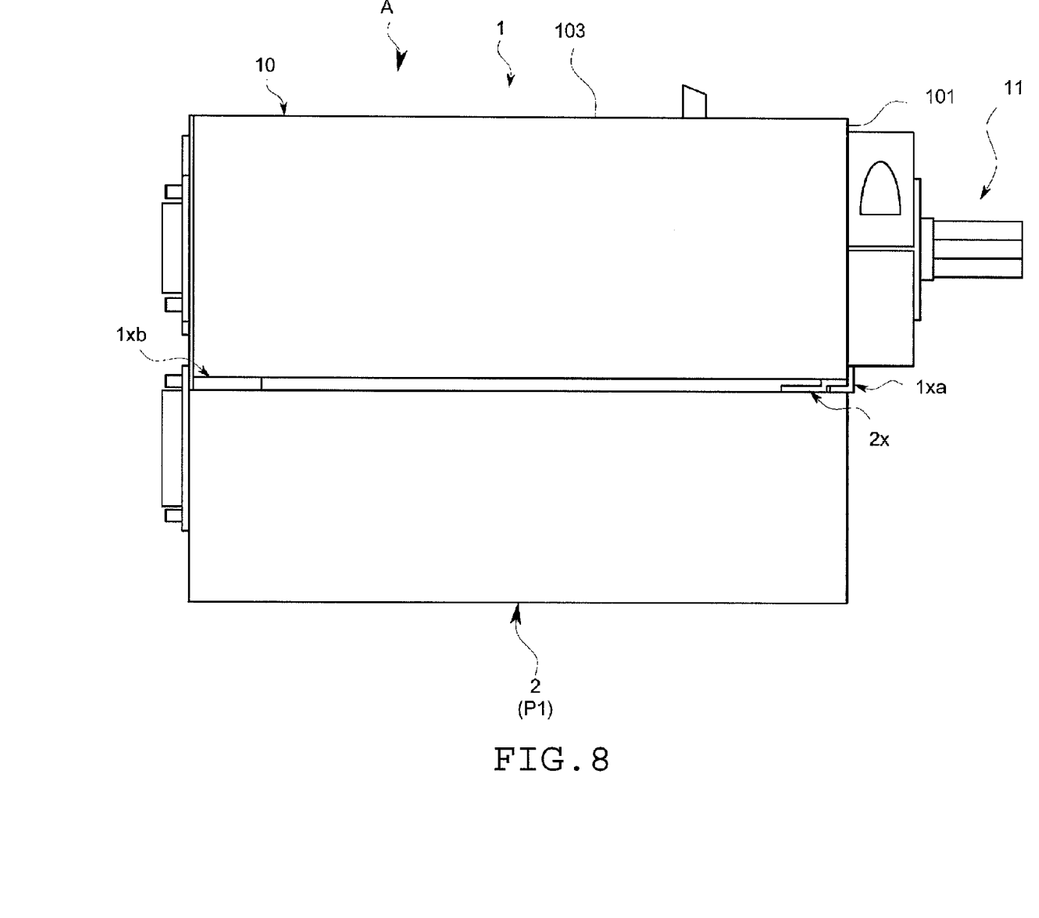
FIG. 8 is a rear view illustrating the residual gas analyzer in the same embodiment.

Also, when the sensor unit 1 is mounted, a top wall 103 of the sensor unit case 10 and a top face panel 203 of the device main body 2 are adapted to be substantially level with each other (see FIGS. 4 and 6), and the side wall 101 of the sensor unit case 10 and a left side panel 204 of the device main body 2 are adapted to be substantially level with each other (see FIG. 5). That is, when the sensor unit 1 is mounted on the device main body 2, the residual gas analyzer A is of a substantially rectangular parallelepiped shape as a whole except for a tip part of the sensor part 11.

Figure 3:
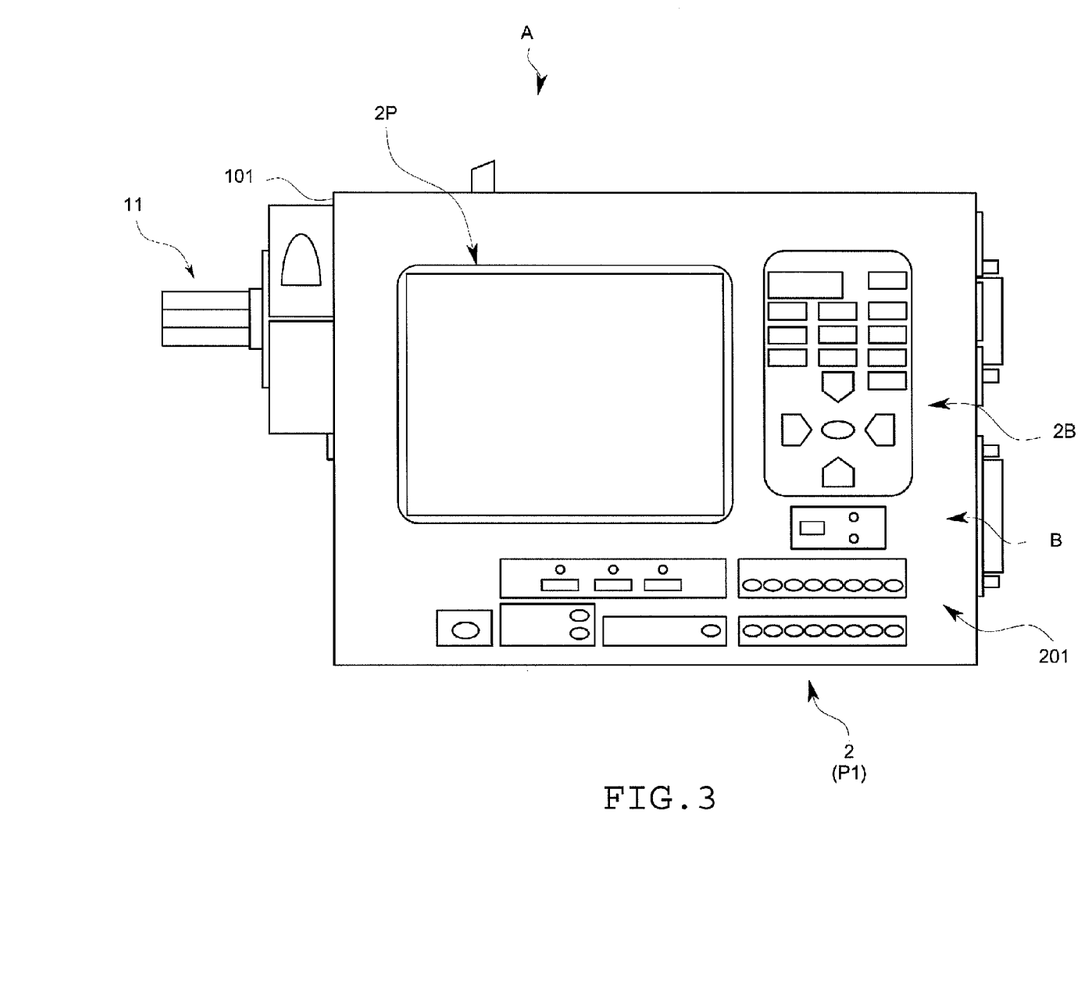
FIG. 3 is a front view illustrating the residual gas analyzer in the same embodiment.
Figure 4:
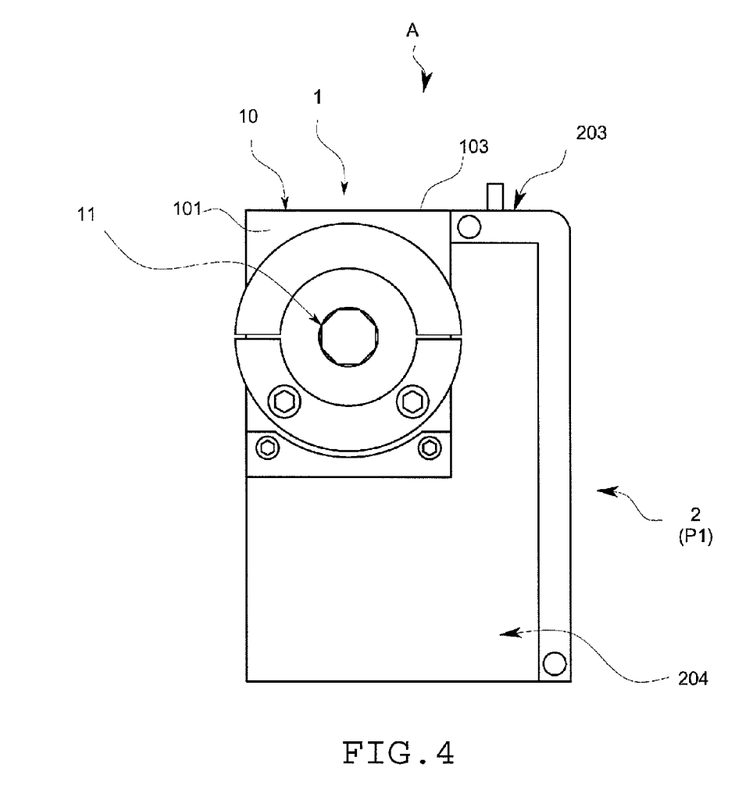
FIG. 4 is a left side view illustrating the residual gas analyzer in the same embodiment.

The front panel 201 is configured to have a liquid crystal panel 2P (corresponding to "an analysis processing result screen display part for displaying on a screen a result of the analysis processing in the residual gas analysis processing part" of the present invention) and the like, in addition to having a plurality of operation buttons 2B. The plurality of operation buttons 2B include sensor operation buttons (corresponding to "an operating part" of the present invention) for receiving an operation for controlling the sensor part 11, display buttons for operating a display mode, and the other buttons.

Figure 10:
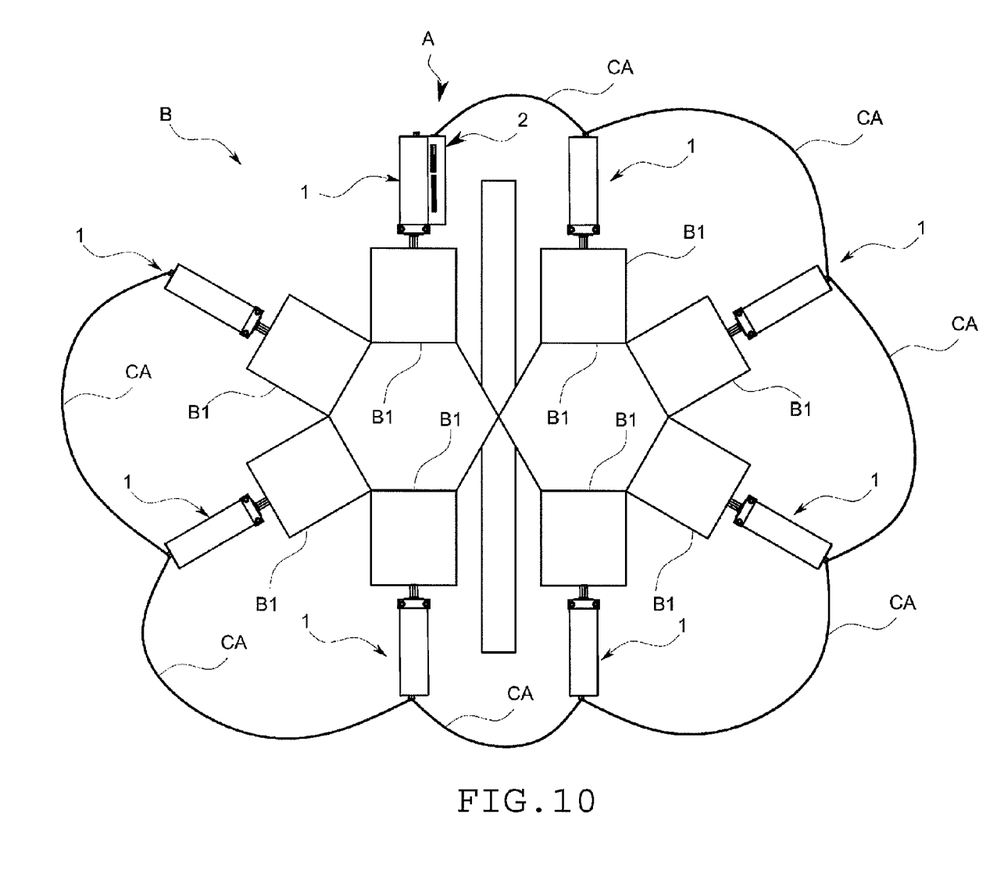
FIG. 10 is a diagram illustrating a connection aspect of a plurality of sensor units in the same embodiment.

The right side panel 202 is provided with a power supply switch 2S, a connector 2C for making a cable-connection to the sensor unit 1 being removed from the device main body 2, and the like. In the present embodiment, as the connector 2C, an RS-232C connector is used, but may be appropriately changed depending on an embodiment, such as the use of a USB connector. By using the connector 2C, the one device main body 2 is adapted to be serially connected with the eight sensor units 1 by a cable CA connection (see FIG. 10). Specifically, one of the eight sensor units 1 is adapted to be mounted on the device main body 2, and the other seven sensor units 1 are adapted to be sequentially and serially connectable to the one sensor unit 1 with being removed from the device main body 2. This enables, for example, the eight sensor units 1 to measure and control inside states of eight chambers B1 of a semiconductor equipment B at once.

Also, on a mounting surface 200 for mounting the sensor unit 1, mounting brackets 2x respectively having the same cross-sectional shape are provided along a mounting direction (see FIG. 2).

Next, the usage of the residual gas analyzer A having the above configuration is described.

Case (1): the sensor unit 1 is used with being removed from the device main body 2.

First, the sensor unit 1 is removed from the device main body 2.

Then, a cable CA connection between the removed sensor unit 1 and the device main body 2 is made (see FIG. 2).

Subsequently, the removed sensor unit 1 is fitted to a measurement position of the semiconductor equipment.

The sensor operation buttons of the device main body 2 are operated to start a measurement.

When the measurement is started, the ion source 111 in the sensor part 11 first ionizes gas molecules. Then, an ion beam obtained from the ion source 111 is accelerated and converged by the lens 112, and the ion beam accelerated and converged by the lens 112 is separated by the quadrupole part 113 according to an ion's mass/charge ratio. The ion beam separated in the quadrupole part 113 is captured and detected as an ion current by the Faraday cup detection part 114.

Subsequently, the spectraconverter part 12 converts the ion current detected in the Faraday cup detection part 114 into a digital voltage signal indicating a voltage value, and transmits the signal to the device main body 2 as measurement data.

The measurement data obtained in this manner is subjected to analysis processing by the residual gas analysis processing part of the device main body 2, and a result of the analysis processing can be displayed on the liquid crystal panel 2P by an operation of the display buttons, or the like.

In addition, the data obtained by the measurement can be temporarily or semipermanently stored in the internal memory.

Case (2): the sensor unit 1 is used with being mounted on the device main body 2.

Operations are the same as in Case (1) except that the sensor unit 1 is used with being mounted on the device main body 2 and fitted to the measurement position. However, the device main body 2 may also be fitted to the sensor unit 1 after the sensor unit 1 has been fitted to the semiconductor equipment B. As described, even if the sensor unit 1 and the device main body 2 are separately and sequentially fitted with respect to the semiconductor equipment B, the device main body 2 is of the substantially L-block shape as viewed from outside, and therefore can be easily fitted to the sensor unit 1 of the substantially rectangular parallelepiped shape. In addition, because the mounting brackets 1x and those 2x respectively having the same cross-sectional shapes are provided in the mounting direction between the sensor unit 1 and the device main body 2, the sensor unit 1 and the device main body 2 can be easily fitted to each other while being slid. Also, after the sensor unit 1 and the device main body 2 have been fitted to each other, they do not rattle in a direction orthogonal to the mounting direction because of the presence of the mounting brackets 1x and 2x.

Therefore, according to such residual gas analyzer A, if the sensor unit 1 is removed from the device main body 2, it can be arranged and used in a small area of the semiconductor equipment, which cannot contain the device as a whole. On the other hand, if the sensor unit 1 is mounted on the device main body 2, the device can be independently used as a whole, and is therefore easy to handle. Also, the device does not require activation of an external device such as a personal computer to operate the sensor part 11, and is therefore convenient.

That is, there can be provided the excellent gas analyzer A, which can make a measurement with being suitably arranged even in the small area of the semiconductor equipment, or the like, and without an external personal computer, perform operations from the measurement to a display of a result of the measurement.

The sensor unit 1 includes the spectraconverter part 12 for converting the ion current detected in the Faraday cup detection part 114 into the digital voltage signal indicating a voltage value, so that even if the sensor unit 1 is used with being removed from the device main body 2, the effect of, for example, a magnet or the like provided in the semiconductor equipment can be avoided, and therefore the measurement can be made with accuracy.

Note that the present invention is not limited to the above-described embodiment.

For example, in the present embodiment, the operating part is configured to be the operation buttons 2B, but may be configured to be of a touch panel type using the liquid crystal panel 2P.

Also, in the present embodiment, the analysis processing result is adapted to be displayed on the liquid crystal panel 2P; however, as long as the residual gas analyzer A is used as a standalone with being separated from an external device such as a personal computer, an output mode of the analysis processing result may be changed depending on an embodiment. For example, a printing out of the analysis processing result is allowed.

Further, the eight sensor units 1 are adapted to be serially connectable to the one device main body 2 by the cable connection; however, the number of the sensor units 1 to be connected may be appropriately changed. Also, instead of the cable connection, a wireless connection may be employed.

Figure 11:
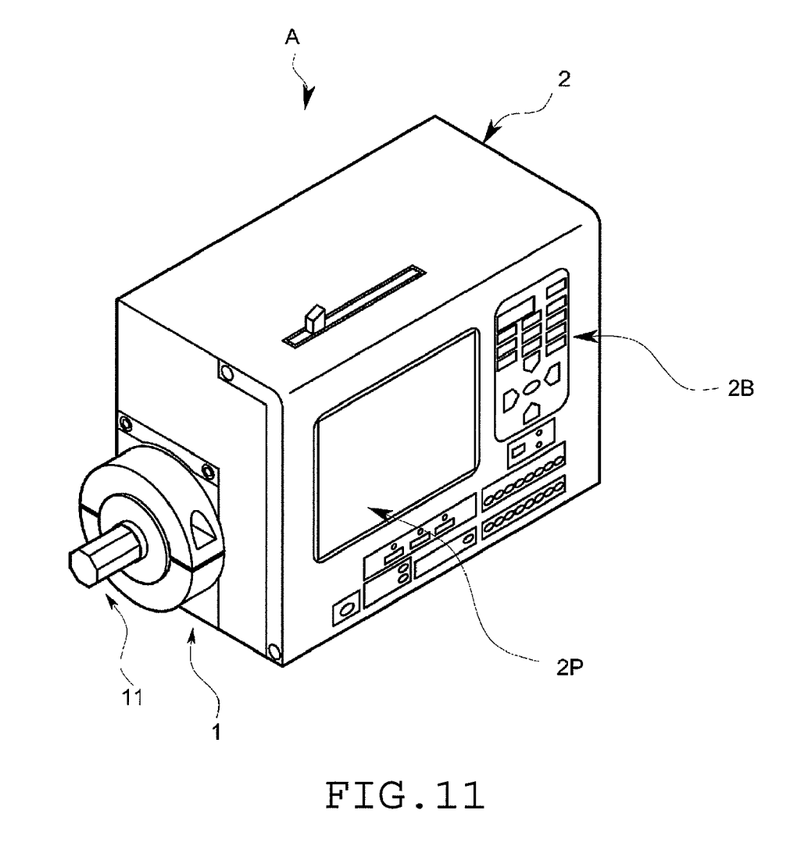
FIG. 11 is an overall perspective view illustrating a residual gas analyzer (mounted status) in another embodiment of the present invention.
Figure 12:
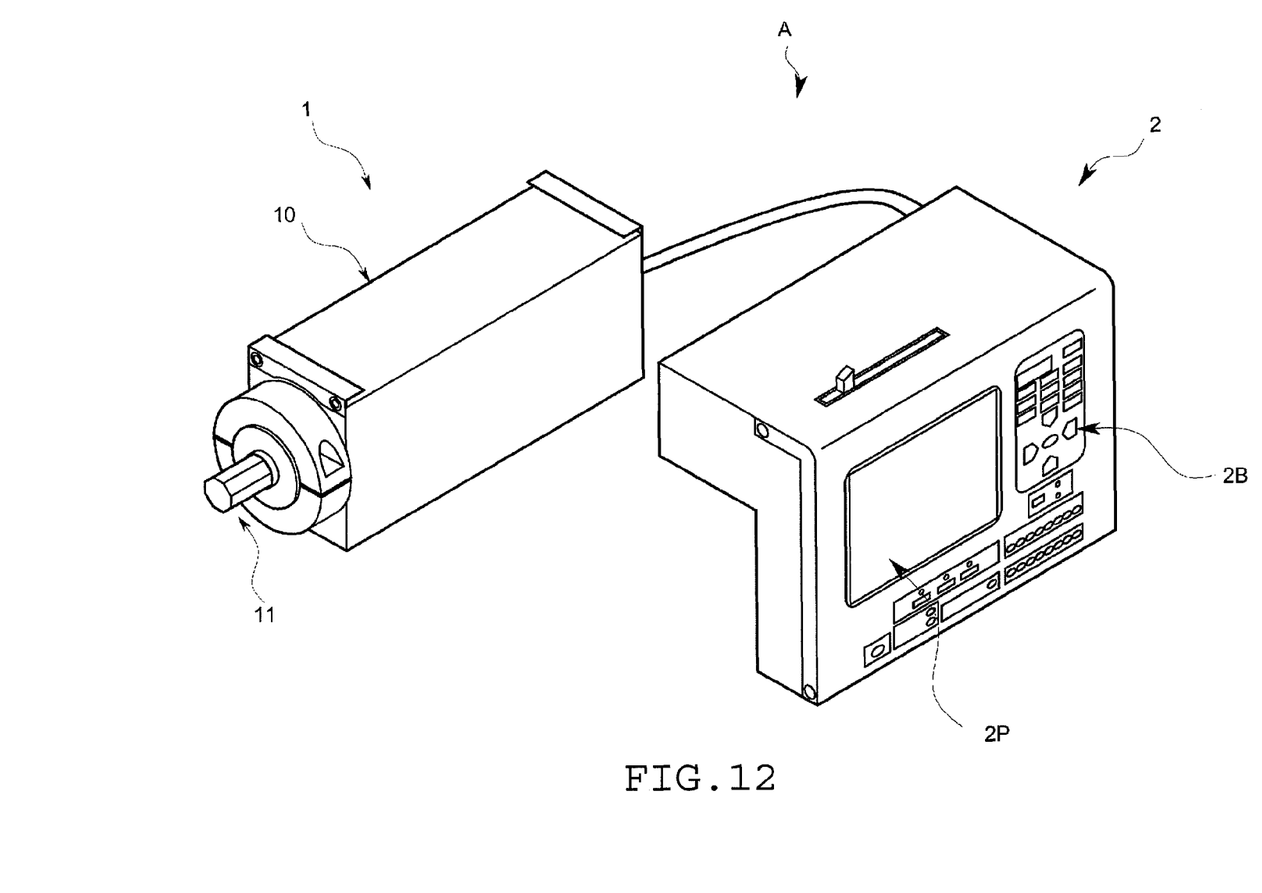
FIG. 12 is an overall perspective view illustrating the residual gas analyzer (removed status) in the same embodiment.

Still further, as illustrated in FIGS. 11 and 12, there may be an embodiment in which the sensor unit 1 fits and supports the device main body 2.

Figure 13:
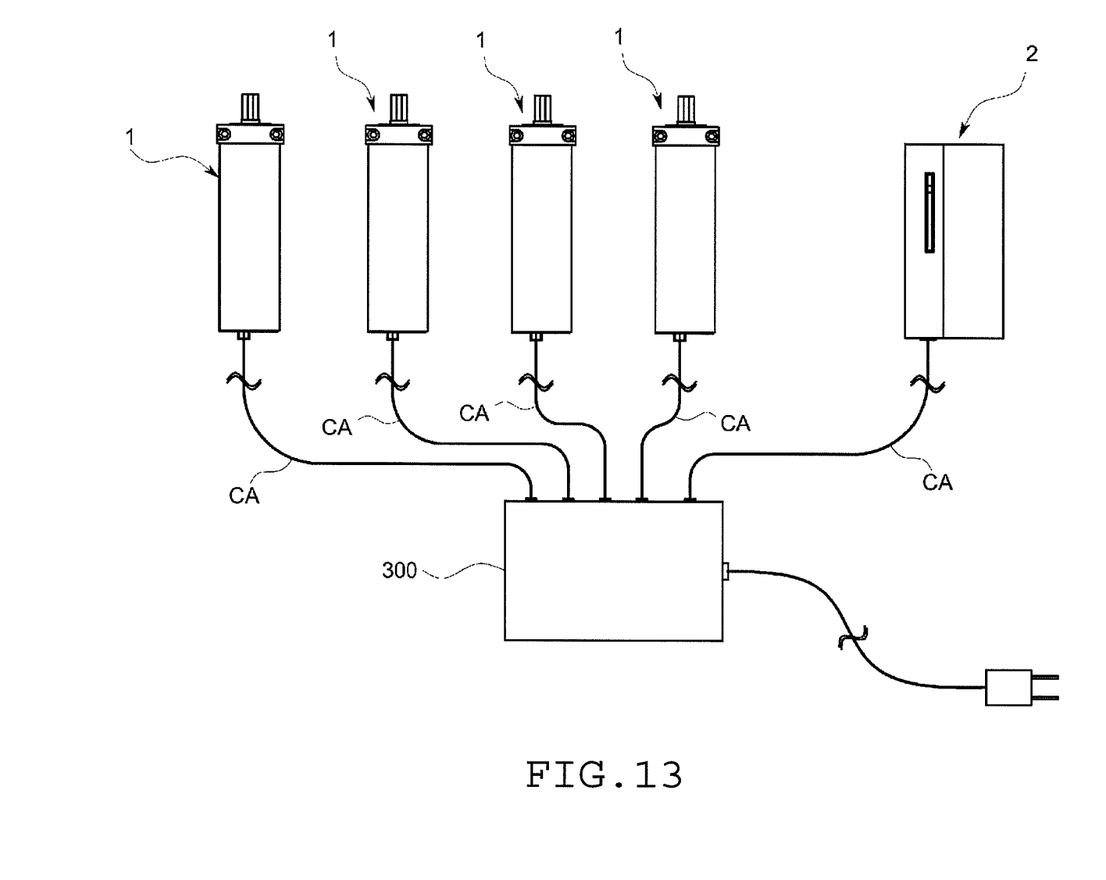
FIG. 13 is an overall configuration diagram illustrating a residual gas analyzer in still anther embodiment.

In addition, as illustrated in FIG. 13, a plurality of sensor units 1 and the one device main body 2 may be adapted to be connected to one hub 300 (a so-called hub power supply) capable of supplying power. Specifically, each of the sensor units 1 has the cable CA capable of supplying power and making communication, and the cable CA is connected to the hub 300. Also, the device main body 2 has the cable CA capable of supplying power and making communication, and the cable CA is connected to the hub 300. Based on this, even if the plurality of sensor units 1 are used, wiring can be simplified.

Figure 14:
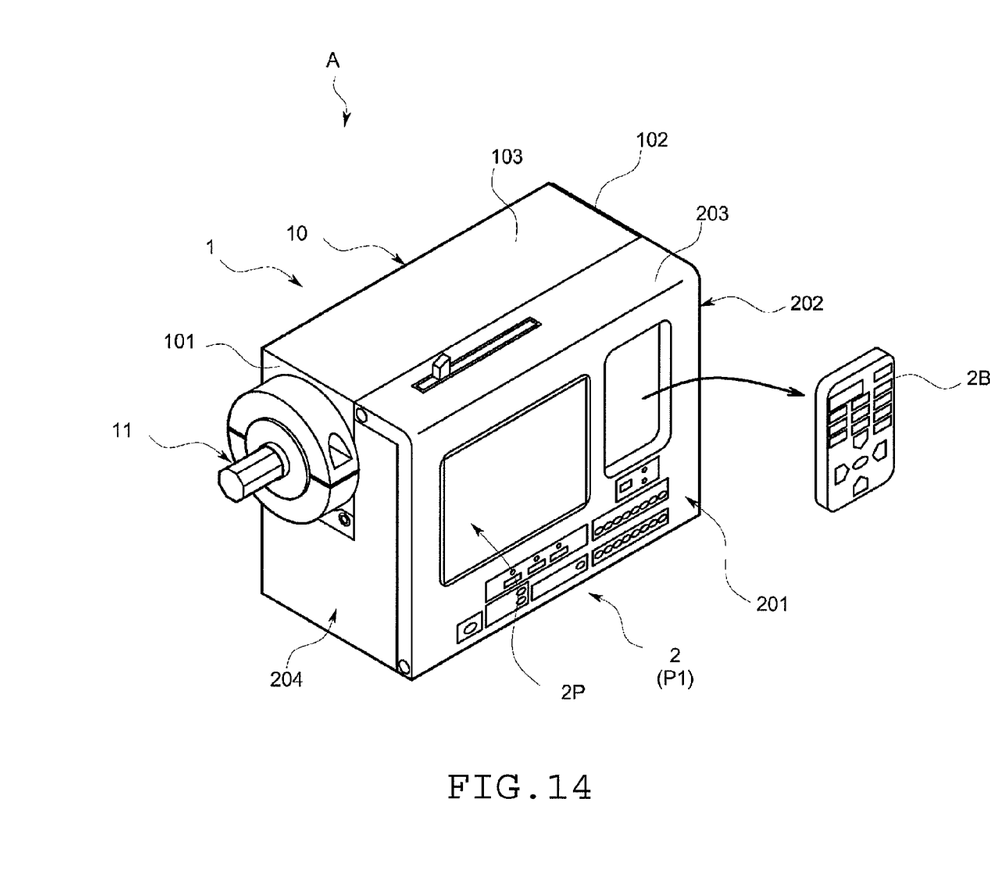
FIG. 14 is an overall perspective view illustrating a residual gas analyzer (mounted status) in yet another embodiment.

Further, as illustrated in FIG. 14, the operating part 2B may be configured to be removable from the device main body 2. This enables usability of the residual gas analyzer to be further improved. Specifically, the plurality of operation buttons 2B are adapted to be removable as a remote control from the front panel 201 in the embodiment. In addition, an operating remote control may be provided, separately from the device main body. In this case, the operating remote control may be wireless or wired.

Besides, a specific configuration of each of the parts is also not limited to the above-described embodiment, but may be variously modified without departing from the scope of the present invention.

INDUSTRIAL APPLICABILITY

According to the present invention, if a sensor unit is removed from the device main body, it can be arranged and used in the small area of the semiconductor equipment, which cannot contain the device as a whole. On the other hand, if the sensor unit is mounted on the device main body, the device can be independently used as a whole, and is therefore easy to handle. Also, the device does not require activation of an external device such as a personal computer to operate the sensor part, and therefore can be convenient.

We claim:

1. A residual gas analyzer comprising:
a sensor unit including a sensor part for measuring a residual gas in an equipment or a residual gas from the equipment, the equipment having a chamber; and
a device main body provided with an operating part for receiving an operation for controlling the sensor part, a residual gas analysis processing part for performing analysis processing of the measured residual gas on a basis of an output of the sensor part, and an analysis processing result screen display part for displaying on a screen a result of the analysis processing in the residual gas analysis processing part, wherein:
the device main body has a mounting surface for mounting the sensor unit;
in a mounted status where the sensor unit is mounted on the mounting surface, the device main body controls the sensor part to perform the analysis processing of the measured residual gas; and
in a removed status where the sensor unit is removed from the mounting surface, the device main body controls the sensor part to perform the analysis processing of the measured residual gas.

2. The residual gas analyzer according to claim 1, wherein one of a plurality of sensor units is mounted on the device main body; and the other sensor units are connected by wire or wireles sly to the device main body or one sensor unit described above so as to form a serial or parallel connection, while being removed from the device main body described above.

3. The residual gas analyzer according to claim 1, wherein the sensor part is provided with: an ion source for ionizing gas molecules; a quadrupole part for separating an ion beam obtained from the ion source, according to an ion's mass/charge ratio; and a Faraday cup detection part for capturing the ion beam separated in the quadrupole part to detect as an ion current.

4. The residual gas analyzer according to claim 3, wherein the sensor unit is provided with a spectraconverter part for converting the ion current detected in the Faraday cup detection part into a digital voltage signal indicating a voltage value.

5. The residual gas analyzer according to claim 1, wherein the operating part is an operation button provided in the device main body.

6. The residual gas analyzer according to claim 1, wherein the operating part is removable from the device main body.

7. The residual gas analyzer according to claim 2, wherein the device main body and the plurality of sensor units described above are connected to a hub capable of supplying power.

* * * * *